United States Patent [19]

Arndt et al.

[11] Patent Number: 5,149,850
[45] Date of Patent: Sep. 22, 1992

[54] PROCESS FOR THE PRODUCTION OF HIGH-PURITY TETRACHLORO-1,4-BENZOQUINONE

[75] Inventors: Otto Arndt, Hofheim am Taunus; Theodor Papenfuhs, Frankfurt am Main, both of Fed. Rep. of Germany

[73] Assignee: Hoechst Aktiengesellschaft, Frankfurt am Main, Fed. Rep. of Germany

[21] Appl. No.: 726,625

[22] Filed: Jun. 28, 1991

Related U.S. Application Data

[63] Continuation of Ser. No. 151,883, Feb. 3, 1988, abandoned.

[30] Foreign Application Priority Data

Feb. 6, 1987 [DE] Fed. Rep. of Germany ....... 3703566
Mar. 6, 1987 [DE] Fed. Rep. of Germany ....... 3707148

[51] Int. Cl.$^5$ .................... C07C 50/24; C07C 46/06
[52] U.S. Cl. ...................................... 552/308; 568/765
[58] Field of Search ........................................ 552/308

[56] References Cited

U.S. PATENT DOCUMENTS

| | | | |
|---|---|---|---|
| 2,414,008 | 1/1947 | Alquist | 552/308 |
| 2,422,089 | 6/1947 | Fletcher | 552/308 |
| 2,422,229 | 6/1947 | Fletcher | 552/308 |
| 2,722,537 | 11/1955 | Fox | 552/308 |

*Primary Examiner*—Vivian Garner
*Attorney, Agent, or Firm*—Connolly & Hutz

[57] ABSTRACT

A process for the production of high-purity tetrachloro-1,4-benzoquinone by the action of chlorine and hydrochloric acid on hydroquinone which comprises causing 1.9 to 2.1 times the molar quantity of gaseous chlorine to act at temperatures from 5° to 15° C. on 1 mol of hydroquinone in 6 to 7 times the molar quantity of 30 to 37% hydrochloric acid, then diluting the resulting suspension, essentially containing 2,5-dichlorohydroquinone, with 2 to 3 parts of water, relative to hydroquinone employed, and initially warming to a temperature from 20° to 30° C., subsequently introducing 1.9 to 2.1 times the molar quantity of chlorine gas in an air atmosphere while raising the temperature to 90°–100° C. with simultaneous dilution with 3.5 to 4.5 parts of water, relative to hydroquinone employed, and finally introducing 1 to 2 times the molar quantity of gaseous chlorine, relative to hydroquinone employed, at temperatures from 100° to 115° C.

4 Claims, No Drawings

PROCESS FOR THE PRODUCTION OF HIGH-PURITY TETRACHLORO-1,4-BENZOQUINONE

CROSS REFERENCE TO RELATED APPLICATION

This is a continuation of copending U.S. application Ser. No. 07/151,883 filed Feb. 3, 1988, now abandoned.

DESCRIPTION

The present invention relates to a process for the production of high-purity tetrachloro-1,4-benzoquinone (designated "chloranil" below) from hydroquinone.

BACKGROUND OF THE INVENTION

The production of chloranil from hydroquinone (1,4-dihydroxybenzene) or 1,4-benzoquinone or chlorinated 1,4-benzoquinone by the following processes, described in the literature, is known per se:

1. Chlorination of hydroquinone with concentrated hydrochloric acid and concentrated hydrogen peroxide in the presence of magnesium chloride (German Offenlegungsschrift 2,645,114);
2. Action of chlorine on hydroquinone in boiling concentrated hydrochloric acid (Chemiker Zeitung 56 (1932), page 569);
3. Action of hydrochloric acid and nitric acid (aqua regia) on hydroquinone (J. Chem. Soc. Japan 63 (1942), page 1441);
4. Reactions of antimony(V) chloride with hydroquinone (Chemiker Zeitung 104 (1980) No. 1, pages 13 and 14;
5. Action of hydrogen chloride, air and metal salts on hydroquinone (East German Pat. No. 29,292);
6. Reaction of trichloro-1,4-benzoquinone with chlorine in the presence of iodine and water (Liebigs Annalen der Chemie, supplementary volume 6 (1867), 213);
7. Treatment of a mixture of trichloro-1,4-benzoquinone and tetrachloro-1,4-benzoquinone with hydrogen chloride in glacial acetic acid and subsequent action of concentrated nitric acid (Beilstein 7, 637);
8. Action of concentrated hydrochloric acid and 35% hydrogen peroxide on 1,4-benzoquinone (Ann. Chimica applic. 22 (1932), 602;
9. Introduction of chlorine into a solution of hydroquinone in aqueous hydrochloric acid with added chromium trioxide (Naugatuck Chem. Comp., USA, German Pat. No. 594,520, Friedländer 20, 2047, U.S. Pat. No. 1,918,328).

These known processes have, however, the following disadvantages:

Re 1: A very large excess of hydrochloric acid (96 times the molar quantity) is required, and a very high salt load results due to the addition of 7.4 times the molar quantity of magnesium chloride. Furthermore, the prescribed temperature/time control during the addition of hydrogen peroxide cannot be maintained because of the high heat of reaction. A repeat of this process using only 30 times the molar quantity of hydrochloric acid, 3 times the molar quantity of magnesium chloride and more suitable temperature control gave a qualitatively poor chloranil (melting point 215°-220° C., yield 95% of theory) with trichloro-1,4-benzoquinone and tetrachlorohydroquinone as impurities.

Re 2: The introduction of gaseous elementary chlorine into boiling concentrated hydrochloric acid leads to an extensive escape of elementary chlorine gas into the hydrogen chloride vapors and makes it necessary to use a large excess of chlorine.

The possibility of working under pressure (in an autoclave), not indicated in the quoted literature reference, requires greater engineering and safety efforts (fully enameled fittings, valves and pipe connections).

The quantity of 37% hydrochloric acid indicated there (28 times the molar quantity) is very high, but is evidently insufficient for obtaining a reaction mixture which can be stirred at 25° C. Under these conditions, the mixture solidifies with the formation of tetrachlorohydroquinone.

Re 3: In this process, about 25 times the molar quantity of mineral acid, composed of 15 times the molar quantity of hydrochloric acid and about 10 times the molar quantity of nitric acid, is used. The yield is only about 45-65% of theory (melting point 280° C.). There is no indication regarding the disposal of the excess acid (in particular of the nitric oxides).

Re 4: The use of antimony is toxicologically objectionable and requires expensive recovery. Moreover, phosgene is said to be formed in this process.

Re 5: In the cited patent itself, attention is drawn to the high consumption of auxiliaries and to the low yield. Moreover, the steam distillation consumes a lot of energy.

Re 6: The use of iodine makes the regeneration of the hydrochloric acid for re-use more difficult.

Re 7: The stagewise synthesis from quinone (here: trichloro-1,4-benzoquinone) and hydrochloric acid with subsequent oxidation (here: nitric acid) of the chlorinated hydroquinone (here: tetrachlorohydroquinone) to give the quinone, with the necessary interstage purification operations, is an extremely time-consuming process and is unsuitable as an industrial process.

Re 8: In the process, an initial treatment with concentrated hydrochloric acid (22 Bé =37%) (11 times the molar quantity) for 20 hours is followed by a treatment with 35% hydrogen peroxide below 60° C. for 12 hours. Even though a high yield of chloranil (melting point 289° to 290° C.) is obtained, the production becomes very expensive because of the low space-time yield).

Re 9: In the process, hydroquinone in hydrochloric acid is oxidized with chromium (VI) oxide (20 g/mol) to quinhydrone and the latter is then chlorinated with elementary chlorine to chloranil, initially at 25° C. and finally while hot. In the light of the present demands for protection of the environment, the use of chromium (VI) oxide is no longer tolerable economically.

The above review of the state of the art shows that the known processes generally require a large excess of hydrochloric acid, in some cases even auxiliaries which pollute the environment, and unusual oxidizing agents as well as long reaction times.

SUMMARY OF THE INVENTION

It has now been found, surprisingly, that the consumption of materials (especially of hydrochloric acid and chlorinating agent) and the time taken can be considerably reduced and, moreover, a high-purity product can be obtained, when the chlorination and oxidation are weighted in terms of time and temperature in such a way that oxidation to quinhydrone or quinone is avoided until 2 chlorine atoms have been introduced, so that the introduction of the third chlorine atom takes place simultaneously with the oxidation to trichlorobenzoquinone.

The invention thus relates to an improved process for the production of high-purity tetrachloro-1,4-benzoquinone by causing 1.9 to 2.1 times and preferably twice the molar quantity of gaseous chlorine to act at temperatures from 5° to 15° C. on 1 mole of hydroquinone (molecular weight 110.1) in 6 to 7 times the molar quantity of 30 to 37% hydrochloric acid, then diluting the resulting suspension, essentially containing 2,5-dichlorohydroquinone, with 2 to 3 parts of water, relative to hydroquinone employed, and initially warming to a temperature from 20 to 30° C., subsequently introducing 1.9 to 2.1 times and preferably twice the molar quantity of chlorine gas in an air atmosphere while raising the temperature to 90°–100° C. with simultaneous dilution with 3.5 to 4.5 and preferably 4 parts of water, relative to hydroquinone employed, and finally introducing 1 to 2 times the molar quantity of gaseous chlorine, relative to hydroquinone employed, at temperatures from 100° to 115° C.

DETAILED DESCRIPTION

The reason for the improved process control is the exploitation of the higher solubilities of the monochlorinated to trichlorinated hydroquinones in the concentrated hydrochloric acid as compared with the corresponding monochlorinated to trichlorinated 1,4-benzoquinones.

Departures from the process according to the invention manifest themselves in an increased consumption of chlorinating agent and a poor quality of the chloranil (higher content of tetrachlorohydroquinone, 2,3- and 2,5-dichloro-1,4-benzoquinone, trichloro-1,4-benzoquinone and unknown secondary components) (detected by HPLC = high-performance liquid chromatography and HPTLC = high-performance thin-layer chromatography).

The more rapid reaction with the chlorinating agent due to the higher solubilities of the monochlorinated to trichlorinated hydroquinones is further assisted by the use of surface-active auxiliaries which are stable to acid and chlorine, and these also effectively suppress possible foaming of the reaction mixture. A secondary alkanesulfonate or an antifoam based on fluorinated anions is suitable as such an auxiliary. The surface-active auxiliaries are advantageously used in a quantity of about 5 to 15 millimol per mol of hydroquinone employed. The concentration of the hydrochloric acid is also of great importance, particularly at the start of the chlorination. At starting hydrochloric acid concentrations below 30%, highly colored reaction mixtures are obtained, which finally give poor quality chloranil. An adequately high starting hydrochloric acid concentration lowers the reduction potential of the hydroquinones to such an extent that, in line with the purpose of the invention, they remain protected from premature oxidation to 1,4-benzoquinone until the third chlorine atom has been introduced.

The hydrochloric acid concentration increases during the conversion, so that it is necessary to dilute with water during the reaction, which advantageously is carried out by means of a defined temperature, time and addition program. As a result of the dilution, the quantity of hydrochloric acid to be employed can be considerably reduced, the reaction mixture remains stirrable and an emission of elementary chlorine before the end of the conversion is prevented. Passing air through, starting at 50° C., promotes the oxidation to chlorinated p-benzoquinone.

As compared with the state of the art, the process according to the invention is economically and ecologically advantageous. The mother liquors are regenerated by distillation to give 20% hydrochloric acid. The regenerated acids are colorless, and contain at most traces of organic carbon and can be re-used at other points in the production. Apart from the wash filtrate and a distillation residue composed essentially of secondary alkanesulfate, no further production residues, which have to be disposed of, are obtained.

The chloranil produced according to the invention is of high purity, as demonstrated by the melting point (281°–282° C.) and by the fact that it does not contain any tetrachlorohydroquinone.

| | |
|---|---|
| C content: | 29.3–29.7% (theoretically 29.31%) |
| Cl content: | 57.3–57.6% (theoretically 57.67%) |
| Purity (by titanometry) = | 100.0% |

A preferred embodiment of the process according to the invention will now be given, parts being parts by weight:

1 part of hydroquinone is initially reacted at 10° C. with only about 1.3 parts of chlorine gas (twice the molar quantity) in 6.3 parts of 31% hydrochloric acid (corresponding to 6 times the molar quantity, relative to the hydroquinone employed) in the presence of about 0.025 part of secondary alkanesulfonate. The reaction is highly exothermic. A thick, light beige-colored suspension is formed. The suspension is then diluted with about 2 parts (relative to hydroquinone) of water and warmed to 25° C. The reaction product formed by this time has the following composition:

64 mol % of 2,5-dichlorohydroquinone,
23 mol % of 2,3-dichlorohydroquinone and
13 mol % of 2-chlorohydroquinone.

During further heating up to 95° C., advantageously while passing air through, about a further 1.3 parts of chlorine (twice the molar quantity, relative to hydroquinone employed) are introduced as gas. At the same time, the mixture is diluted with about 4 parts of water (relative to hydroquinone employed). The color of the suspension changes to light yellow.

The last mol of chlorine, still necessary, is introduced as a gas at 105° C. with simultaneous addition of about 4 parts of water (relative to hydroquinone employed) and while passing air through. In total, about 5.3 mol of chlorine are introduced as gas. An off-gas (about 20 mol %, relative to hydroquinone), corresponding to the chlorine excess employed, is not evolved until towards the end of the chlorine addition. The off-gas does not contain any hydrogen chloride. After filtration and washing, pure chloranil is obtained in a yield of 98% of theory, relative to hydroquinone employed.

The approximately 20 % mother liquor is reprocessed to give distilled 20 % hydrochloric acid (organic carbon = 69 mg/l).

The only production residues obtained are the secondary alkanesulfonate used (distillation residue from the hydrochloric acid regeneration) and the wash filtrate. The latter can be purified biologically (residual COD = 3.7 kg of oxygen (O$_2$) per ton of chloranil).

Chloranil is a valuable intermediate for the production of dyes and pesticides. It is also used as a photochemical and vulcanizing agent, and serves as lubricant additive.

The examples which follow and the comparison examples indicated serve to illustrate the invention in more detail.

EXAMPLE 1

73 parts of chlorine gas (1.0 mol) are introduced within 120 minutes at 10° C. with external cooling into a mixture of 353 parts of 31% hydrochloric acid (3.0 mol), 55.6 parts of hydroquinone (0.5 mol) and 1.4 parts of secondary n-alkanesulfonate. The mixture is then stirred for a further 30 minutes at 10° C. Subsequently, the thick, light beige-colored suspension is diluted with 100 parts of water and warmed to 25° C. within 60 minutes.

A further 73 parts of chlorine gas (1.0 mol) are then introduced within 210 minutes, 200 parts of water being added dropwise at the same time and the mixture being simultaneously heated up to 95° C. Starting at about 50° C., air is passed through at the same time until the end of the reaction.

18 parts (0.25 mol) of chlorine gas are introduced within 60 minutes into the now light yellow, non-foaming suspension, 40 parts of water being added dropwise at the same time and the mixture being simultaneously heated up to 105° C. Stirring is then continued for 300 minutes at 105° C., during which time a maximum of 26 parts of chlorine gas (0.37 mol) must still be introduced, depending on the progress of conversion (the progress of the chlorination and oxidation is followed by HPTLC). At the same time, 160 parts of water are added dropwise (heating bath 115° C.).

The chlorination time is 13.5 hours. 190 parts of chlorine gas (2.7 mol) are introduced in total. After the end of the reaction, the residual chlorine gas present in the reactor atmosphere is flushed into a receiver containing 250 parts of water and 125 parts of 33% sodium hydroxide solution (0.10 mol of CL$_2$). The off-gas does not contain any hydrogen chloride.

After filtration at 90° to 95° C. and washing with 500 parts of water, this gives 121 parts of pure yellow chloranil (0.49 mol).

| | |
|---|---|
| C content: | 29.3–29.7% (theoretically 29.31%) |
| Cl content: | 57.3–57.6% (theoretically 57.67%) |
| Purity (by titanometry) = | 100% |
| Melting point: | 281–282° C. |

The mother liquor (996 parts of about 20% hydrochloric acid) is distilled down to a residue under normal pressure. This gives 960 parts of 20% hydrochloric acid (colorless, organic carbon = 69 mg/l) and 5.1 parts of distillation residue which can be removed from the distillation flask by means of water. The wash filtrate is biodegradable.

EXAMPLE 2

Procedure Appropriate to Industrial Use 73 parts of chlorine gas (1.0 mol) are introduced within 4 hours at 10° C. with external cooling and under normal pressure (air) into a mixture of 353 parts of 31% hydrochloric acid (3.0 mol), 55.6 parts of hydroquinone (0.50 mol), 0.024 part of iron (III) chloride and 0.3 part of secondary n-alkanesulfonate. The mixture is then stirred for a further 30 minutes at 10° C. Subsequently, the thick, light beige-colored suspension is diluted within about 2 minutes with 400 parts of water, the mixture heating spontaneously to 25° C. 93 parts of chlorine gas (1.3 mol) are then introduced within 4 hours with simultaneous heating to 95° C. This suspension becomes light yellow. No off-gas is formed.

The suspension (HCL content = about 24%) is then diluted with 100 parts of potable water. 14 parts of chlorine gas (0.2 mol) are then introduced within 1 hour into the now light-yellow, non-foaming suspension with simultaneous heating to 105° C. The chlorine gas is introduced in such a way that there is just no escape of off-gas.

Stirring is then continued for 10 hours at 108° C., during which time a maximum of 45 parts of chlorine gas (0.6 mol) must still be introduced, depending on the progress of conversion (the progress of the chlorination and oxidation is followed by HPTLC) (temperature of the heating bath 130° C.). The thin, now lemon-yellow suspension is then stirred for 1 further hour at 108° C.

The chlorination time is 20 hours as a maximum. In total, 225 parts of chlorine gas (3.17 mol) are introduced. The batch is cooled to 90° C. with inert gas blanketing (nitrogen), whereby sucking-back of chlorine from the off-gas absorption is prevented and the atmosphere above the reaction mixture is detoxified. The off-gas stream is taken up in the absorption liquor (45 parts = 0.65 mol). Converted chlorine = 180 parts = 2.54 mol of chlorine (theoretically = 2.50 mol).

After filtration at 90–95° C. and washing with 500 parts of water, this gives 121 parts of pure yellow chloranil (0.49 mol), melting point 293°–295° C.

C content: 29.6% (theoretically 29.31%)
CL content: 57.3% (theoretically 57.67%)
Purity (by titanometry) = 100%
2,3,5,6-tetrachlorohydroquinone not detectable (HPTLC)
2,3,5-trichlorobenzoquinone < 0.5% (HPLC)
Hexachlorobenzene not detectable (GC/MS)

The mother liquor (970 parts) is an approximately 20% hydrochloric acid (5.32 mol of HCL).

EXAMPLE 3

Recycling of Mother Liquor

The procedure followed is as described in Example 2, but with the difference that, in place of the 31% hydrochloric acid, 547 parts of mother liquor (from Example 2, corresponding to 3.0 mol of HCL) are initially introduced. However, after 73 parts of chlorine gas have been introduced within 4 hours at 10° C., only 240 parts of water are used for dilution.

This gives chloranil in the same yield and quality as in Example 2.

The recycling of the mother liquor can be repeated up to about 20 times. This gives chloranil in the same yield and quality, if care is taken to preserve the concentration of the auxiliaries (surfactant and FeCL3) by appropriate further addition and the mother liquor to be used is always corrected to an HCL content of 20%.

COMPARISON EXAMPLE 1

The procedure followed is as described in Example 1, but with the difference that the batch is diluted with 31% hydrochloric acid (587 parts) instead of water. The formation of an off-gas starts already at 50° C.

The progress of conversion is followed by HPTLC.

After 146 parts (2.1 mol) of chlorine gas have been introduced over a period of 7.5 hours, a thick, light beige-colored suspension composed predominantly of tetrachlorohydroquinone, is obtained at the temperature level of 95° C. 21 parts of chlorine were found in the off-gas. After a further 84 parts (1.2 mol) of chlorine gas have been introduced over a period of a further 8 hours, a thin, light yellow suspension is obtained at the temperature level of 105° C., from which 106.4 parts of chloranil having a melting point of 255° to 260° C. are isolated under the working-up conditions according to the example. The chloranil still contains significant amounts of mono-, di- and tetra-chlorohydroquinone.

119 parts of hydrogen chloride and 32 parts of chlorine (0.45 mol of $CL_2$) are found in the off-gas. Higher hydrochloric acid concentrations in the chlorination mixture shift the oxidation of hydroquinone to 1,4-benzoquinone unduly to higher chlorine consumption and higher temperature. The dilution with water is thus an important factor.

COMPARISON EXAMPLE 2

The procedure followed is as described in Example 1, but with the difference that the mixture mentioned there at the beginning contains 228 parts of 20% hydrochloric acid (1.25 mol) instead of 353 parts of 31% hydrochloric acid (3.0 mol).

When chlorine gas is introduced at 10° C., the hydroquinone suspension immediately turns black. After the end of the chlorination with 73 parts of chlorine gas at the temperature level of 10° C., a thick, yellow-greenish suspension is obtained, the color of which changes to light brown when heated to 50° C.

The continuation of the chlorination and working-up according to the example gives 122 parts of chloranil of melting point 242° to 246° C.

Purity (by titanometry) = 76.3%.
C:CL = 6.0:382.

The product is heavily contaminated with monochlorohydroquinone.

COMPARISON EXAMPLE 3

The procedure followed is as described in Example 1, but with exclusion of air (for example under nitrogen). This gives 121 parts of pure tetrachlorohydroquinone as a white powder of melting point 230° to 235° C. The off-gas now contains correspondingly more chlorine (0.50 mol of $CL_2$).

We claim:

1. A process for the production of high-purity tetrachloro-1,4-benzoquinone by the action of chlorine and hydrochloric acid on hydroquinone, which comprises causing 1.9 to 2.1 times the molar quantity of gaseous chlorine to act at temperatures from 5° to 15° C. on 1 mol of hydroquinone in 6 to 7 times the molar quantity of 30 to 37% hydrochloric acid, then in a first dilution step diluting the resulting suspension, essentially containing 2,5-dichlorohydroquinone, with 2 to 3 parts of water, relative to hydroquinone employed, and initially warming to a temperature from 20° to 30° C., subsequently introducing 1.9 to 2.1 times the molar quantity of chlorine gas in an air atmosphere while raising the temperature to 90°-100° C. with simultaneous dilution with 3.5 to 4.5 parts of water, relative to hydroquinone employed in a second dilution step, and finally introducing 1 to 2 times the molar quantity of gaseous chlorine, relative to hydroquinone employed, at temperatures from 100° to 115° C.

2. The process of claim 1, wherein said gaseous chlorine is present in an amount of 2 times the molar quantity of said hydroquinone.

3. The process of claim 1, wherein said water used for dilution is present in the second dilution step in an amount of 4 times the amount of hydroquinone employed.

4. A process for the production of high-purity tetrachloro-1,4-benzoquinone in the presence of a secondary alkanesulfonate by causing 1.9 to 2.1 times the molar quantity of gaseous chlorine to act at temperatures from 5° to 15° C. on 1 mol of hydroquinone in 6 to 7 times the molar quantity of 30 to 37% hydrochloric acid, then in a first dilution step diluting the resulting suspension, essentially containing 2,5-dichlorohydroquinone, with 2 to 3 parts of water, relative to hydroquinone employed, and initially warming to a temperature from 20° to 30° C., subsequently introducing 1.9 t 2.1 times the molar quantity of chlorine gas in an air atmosphere while raising the temperature to 90°-100° C. with simultaneous dilution with 3.5 to 4.5 parts of water, relative to hydroquinone employed in a second dilution step, and finally introducing 1 to 2 times the molar quantity of gaseous chlorine, relative to hydroquinone employed, at temperatures from 100° to 115° C.

* * * * *